United States Patent [19]

Muntwyler et al.

[11] 4,169,896

[45] Oct. 2, 1979

[54] CONTROL OF COCCIDIAL DISEASES BY TREATMENT OF ANIMAL EXCRETA WITH SECONDARY AMINES

[75] Inventors: René Muntwyler, Hofstetten; Clemens Kocher, Therwil, both of Switzerland

[73] Assignee: Ciba-Geigy Corporation, Ardsley, N.Y.

[21] Appl. No.: 884,303

[22] Filed: Mar. 7, 1978

[30] Foreign Application Priority Data

Mar. 9, 1977 [CH] Switzerland ............... 2945/77

[51] Int. Cl.$^2$ .................. A61K 31/13; A01N 9/20; A61L 13/00

[52] U.S. Cl. ................................................... 424/325

[58] Field of Search .................................... 424/325

[56] References Cited

U.S. PATENT DOCUMENTS

| | | | |
|---|---|---|---|
| 3,226,293 | 12/1965 | Ursprung | 424/325 |
| 3,271,247 | 9/1966 | Reinert et al. | 424/325 |
| 4,036,987 | 7/1977 | Thompson et al. | 424/325 |

FOREIGN PATENT DOCUMENTS

| | | |
|---|---|---|
| 1212349 | 3/1966 | Fed. Rep. of Germany . |
| 1528M | 10/1962 | France . |
| 4440M | 9/1966 | France . |

OTHER PUBLICATIONS

Jeney et al.–Chem. Abst., vol. 62, (1965), p. 16806d.

Seveik et al.–Chem. Abst., vol. 71, (1969), p. 2024a.
Danek et al.–Chem. Abst., vol. 73, (1970), 12826u.
Ishizuka et al.–Chem. Abst., vol. 76, (1972), 81003x.

*Primary Examiner*—Sam Rosen
*Attorney, Agent, or Firm*—Frederick H. Rabin

[57] ABSTRACT

Compositions effective against coccidial oocysts and eggs of Ascaris suum, Ascaridia galli and Toxocara canis as active ingredient at least one secondary amine of the general formula I $$R-NH-R' \qquad (I)$$

wherein

R represents a straight-chain or branched alkyl radical of 5 to 18 carbon atoms, a monocyclic cycloalkyl radical or a monocyclic cycloalkylalkyl radical which contains at least 5 carbon atoms in the cyclic moiety, and R' represents a straight-chain or branched alkyl radical of 1 to 9 carbon atoms, a monocyclic cycloalkyl radical of 3 to 6 carbon atoms or a cyclopropylmethyl, cyclohexylmethyl or cyclohexylpropyl radical, and wherein R and R' together contain at least 10 carbon atoms, or a salt thereof with hydrochloric acid or hydrobromic acid or acetic acid or other organic acids, such as lactic, citric, sorbic, undecylenic or glucuronic acid and methods comprising the use of said compositions.

2 Claims, No Drawings

CONTROL OF COCCIDIAL DISEASES BY TREATMENT OF ANIMAL EXCRETA WITH SECONDARY AMINES

DETAILED DISCLOSURE

The present invention relates to anticoccidial and ovolarvicidal compositions which contain secondary amines as active ingredients, and to a method of controlling coccidial and helminthic diseases which comprises the use of said compositions.

Coccidioses are among the most widespread diseases in numerous species of productive livestock, especially in poultry. They are caused by parasitic protozoa of the species Eimeria, for example *Eimeria tenella, Eimeria brunetti, Eimeria maxima, Eimeria necatrix, Eimeria acervulina* etc. Animals attacked by coccidia have a poor increase in weight, with, inter alia, attendant discharge of blood. Coccidioses frequently result in high mortality among poultry. For poultry breeding it is therefore a matter of prime importance to provide suitable compositions for controlling this disease.

A particularly advantageous method of controlling coccidioses consists in killing the oocysts excreted by the host animals. The oocysts are discharged with the excrement of the infected animals and remain viable for a considerable period of time, thus constituting a constant source of new infection.

Helminthioses are also frequently occurring diseases in productive livestock. They are caused by parasitic helminths, for example *Ascaris suum, Ascaridia galli* and *Toxocara canis*. Adult helminths attack mainly the digestive tract of the host animals and their primary stages migrate in the course of their development cycle into other organs, for example the lungs and the liver. Other species of helminths attack organs other than the digestive tract, for example the lungs, heart, kidneys, and the blood.

The eggs of the Ascarididae excreted by the host animals are protected by a thick shell and are very resistant to unfavourable environmental conditions, for example dryness or cold, and also to many chemicals. The eggs can survive for a number of years under suitable conditions and are the most difficult development stages of helminths to combat. However, the prevention of fresh infections caused by assimilation of the worm eggs is of considerable importance, for young animals in particular suffer great harm if the attack is severe.

It has now been found that secondary amines of the general formula I

  (I)

wherein

R represents a straight-chain or branched alkyl radical of 5 to 18 carbon atoms, a monocyclic cycloalkyl radical or a monocyclic cycloalkylalkyl radical which contains at least 5 carbon atoms in the cyclic moiety, and R' represents a straight-chain or branched alkyl radical of 1 to 9 carbon atoms, a monocyclic cycloalkyl radical of 3 to 6 carbon atoms or a cyclopropylmethyl, cyclohexylmethyl or cyclohexylpropyl radical, and wherein R and R' together contain at least 10 carbon atoms, or a salt thereof with hydrochloric acid or hydrobromic acid or acetic acid or with other organic acids, such as lactic, citric, sorbic, undecylenic or glucuronic acid, have an excellent action against coccidial oocysts and eggs of Ascaris suum, Ascaridia galli or Toxocara canis.

Compounds of the formula I which are especially effective for controlling coccidioses and helminthioses are those in which R represents an unbranched alkyl radical of 10 to 12 carbon atoms and R' represents a straight or branched alkyl radical of 1 to 4 carbon atoms or a cyclopropylmethyl radical.

The following compounds have an especially pronounced action:

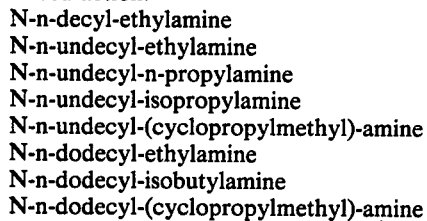

N-n-decyl-ethylamine
N-n-undecyl-ethylamine
N-n-undecyl-n-propylamine
N-n-undecyl-isopropylamine
N-n-undecyl-(cyclopropylmethyl)-amine
N-n-dodecyl-ethylamine
N-n-dodecyl-isobutylamine
N-n-dodecyl-(cyclopropylmethyl)-amine The compounds of the formula I can be obtained in a manner which is in itself known. Thus the compounds of the formula I, wherein R' is as defined in formula I and R represents a straight-chain or branched alkyl radical of 5 to 18 carbon atoms or a monocyclic cycloalkylalkyl radical which contains at least 5 carbon atoms in the cyclic moiety, can be obtained by the method of E. T. Roe, J. T. Scanlan and D. Swern, J. Am. Chem. Soc. 71, 2215 (1949), by reaction of a compound of the formula

wherein $R_1$ represents a straight-chain or branched alkyl radical of 4 to 17 carbon atoms or a monocyclic cycloalkylalkyl radical containing at least 5 carbon atoms in the cyclic moiety, with a compound of the formula

wherein R' is as defined in formula I, and reduction of the resulting compound of the formula

wherein $R_1$ and R' have the above meanings, with lithium alanate as described in Org. Synthesis Coll. Vol. IV, 564, or with sodium acyloxyborohydride in accordance with the method of N. Umino, T. Iwakuma and N. Itoh, Tetrah. Lett. 10, 763—766 (1976).

The compound of the formula I, wherein R is as defined in formula I and R' represents a straight-chain or branched alkyl radical of 2 to 9 carbon atoms or a cyclopropylmethyl, cyclohexylmethyl or cyclohexylpropyl radical, can be obtained for example by the method of E. T. Roe, J. T. Scanlan and D. Swern, J. Am. Chem. Soc. 71, 2215 (1949), by reaction of a compound of the formula

wherein $R_2$ represents a straight-chain or branched alkyl radical of 1 to 8 carbon atoms, a cyclopropyl, cyclohexyl or cyclohexylethyl radical, with a compound of the formula

wherein R is as defined in formula I, and hydrogenation of the resulting compound of the formula

R₂—CONH—R wherein R₂ and R have the above meanings, with lithium alanate as described in Org. Synthesis Coll. Vol. IV, 564, or with sodium acyloxyborohydride in accordance with the method of N. Umino, T. Iwakuma and N. Itoh, Tetrah. Lett. 10, 763—766 (1976).

The compounds of the formula I, wherein R and R' are as defined in formula I, can also be prepared by the method of O. Westphal and D. Jerchel, Berichte 73, 1002 (1940), by reaction of a compound of the formula

R-X wherein R is as defined in formula I and X represents chlorine, bromine or iodine, with a compound of the formula

R'-NH₂ wherein R' is as defined in formula I, or by the method of O. Westphal and D. Jerchel, op. cit., ibid., ibid., by reaction of a compound of the formula

R'-X wherein R' is as defined in formula I and X represents chlorine, bromine or iodine, with a compound of the formula

R-NH₂ wherein R is as defined in formula I.

The invention is illustrated by the following Examples.

EXAMPLE 1

Preparation of N-n-decyl-ethylamine (a) 94.5 g of decylamine were dissolved in 200 ml of pyridine. Then 47.1 g of acetyl chloride were added dropwise at room temperature in the course of 30 minutes to this solution. The mixture was stirred overnight and then poured onto ice-water. The insoluble material was collected by suction filtration, washed neutral and dried in vacuo. Yield: 90 g, m.p. 43°–44° C.

(b) 15.4 g of lithium aluminium hydride were suspended in 300 ml of abs. ether under reflux. 61 g of N-decylacetamide (product of a) were dissolved in 300 ml of ether and the solution was added dropwise in the course of 2 hours to the solution heated to reflux. The heterogeneous mixture was stirred under reflux for 15 hours. Then 32 ml of water were added dropwise at room temperature in the course of 1 hour. After stirring for 30 minutes, the solid was collected by suction filtration and washed repeatedly with ether. The filtrate was evaporated and the residue distilled in a high vacuum. Yield: 35 g of a fraction with a boiling point of 62°–64° C. (0.2 torr).

| | Analysis for C₁₂H₂₇N | | |
|---|---|---|---|
| calculated | C 77.76 % | H 14.68 % | N 7.56 % |
| found | C 77.66 % | H 14.73 % | N 7.44 % |

The following compounds were prepared by a method analogous to one of those described above:

| Compounds | Physical data* |
|---|---|
| N-n-pentyl-n-pentylamine | |
| N-n-hexyl-n-hexylamine | b.p. 113° C. $n_D^{20}$ 1.4340 |
| N-n-octyl-n-octylamine | b.p. 156° C. $n_D^{20}$ 1.4433 |
| N-cyclohexyl-cyclohexylamine | |
| N-n-nonyl-n-nonylamine | b.p. 165° C. $n_D^{20}$ 1.4445 |
| N-n-nonyl-ethylamine | b.p. 99° C. $n_D^{20}$ 1.4339 |
| N-n-nonyl-n-propylamine | b.p. 113° C. $n_D^{20}$ 1.4350 |
| N-3,5,5-trimethylhexyl-ethylamine | b.p. 77° C. $n_D^{20}$ 1.4315 |
| N-n-decyl-ethylamine | b.p. 114° C. $n_D^{20}$ 1.4360 |
| N-n-undecyl-methylamine | b.p. 125-135° C. (20 torr) |
| N-n-undecyl-ethylamine | b.p. 129° C. $n_D^{20}$ 1.4377 |
| N-n-undecyl-n-propylamine | b.p. 142° C. $n_D^{20}$ 1.4392 |
| N-n-undecyl-isopropylamine | b.p. 135° C. $n_D^{20}$ 1.4390 |
| N-n-dodecyl-methylamine | b.p. 134° C. $n_D^{20}$ 1.4406 |
| N-n-dodecyl-ethylamine | b.p. 143° C. $n_D^{20}$ 1.4402 |
| N-n-dodecyl-ethylamine-hydrobromide | m.p. 197-198° C. |
| N-n-dodecyl-n-propylamine | b.p. 156° C. $n_D^{20}$ 1.4421 |
| N-n-dodecyl-isobutylamine | b.p. 161° C. $n_D^{20}$ 1.4408 |
| N-n-dodecyl-cyclopropylmethylamine | b.p. 169° C. $n_D^{20}$ 1.4531 |
| N-cyclododecyl-ethylamine | b.p. 150° C. $n_D^{20}$ 1.4823 |
| N-n-dodecyl-cyclohexylmethylamine | m.p. 130–132° C. (0.1) |
| N-n-dodecyl-3-cyclohexylpropylamine | b.p. 228° C. $n_D^{20}$ 1.4621 |
| N-cyclooctyl-ethylamine | b.p. 89° C. $n_D^{20}$ 1.4729 |
| N-n-tetradecyl-ethylamine | b.p. 168° C. $n_D^{20}$ 1.4450 |
| N-n-undecyl-cyclopropylmethylamine | b.p. 159° C. $n_D^{20}$ 1.4508 |
| N-n-tetradecyl-methylamine | b.p. 162° C. |
| N-n-decyl-methylamine | b.p. 106° C. $n_D^{20}$ 1.4345 |
| N-n-decyl-ethylamine-hydrochloride | m.p. 190° C. |

*b.p. - if not otherwise indicated - at 10 torr

The anticoccidial and ovolarvicidal compositions of the present invention are prepared in a manner known per se by homogeneously mixing and grinding active substances of the formula I with suitable carriers, with or without the addition of dispersants or solvents which are inert to the active substances. The active substances can be formulated and applied as follows:

Solid formulations:

dusts, tracking powders, granules (coated granules, impregnated granules and homogeneous granules);

active substance concentrates which are dispersible in water;

powder mixture;

liquid formulations:

solutions, pastes (emulsions).

The granular size of the carriers for dusts and powder mixtures is advantageously up to approx. 0.1 mm and for granules between 10 and 500 μ (0.01—0.5 mm).

Test of the anticoccidial action on oocysts of Eimeria tenella

Chicks are infected with oocysts of a pure strain of Eimeria tenella. The chicks are sacrificed 7 days later and the oocysts required for testing are taken from the caeca and cleansed by repeated washing in tap water. For sporulation, the oocysts are kept for 4 weeks in potassium bichromate solution. The treatment is carried out by suspending the oocysts in freshly prepared aqueous dilutions of the compositions which have been processed in accordance with galenic principles. Immediately after they have been exposed for 60 minutes on a shaking apparatus, the oocysts are freed from the treatment solution by repeated washing with tap water.

The rate of sporulation is determined microscopically. The action is determined by infecting each of five two-week-old chicks with 100,000 treated oocysts and dissecting the chicks 12 days later. Mortality, the presence of blood in the excrement, oocyst production and intestinal lesions are used as activity parameters.

The test is carried out with unsporulated oocysts (exposure approx. ½ hour after obtention, sporulation after the treatment) and sporulated oocysts (sporulation before the treatment). The tests showed that the active substances have excellent action against coccidial oocysts. No impairment of the state of health of chicks infected with the treated oocysts was observed. There was virtually no production of oocysts.

Ovicidal test on eggs of Ascaris suum

Eggs obtained from the tip of the uterine tube of Ascaris suum are suspended in tap water and sprayed on a slide in an amount of approx. 5000/cm² and allowed to dry.

For tests with non-embryonated eggs, treatment with the substances to be tested is subsequently carried out. For tests with embryonated eggs, the slides with the eggs are kept for 5 weeks at 25° C. in open dishes containing tap water, which is changed 5 times a week, until embryonation has taken place.

For treatment, the substances formulated in accordance with galenic principles are diluted with tap water and the slides containing the eggs are sprayed with a dose of 200 ml/m².

Ordinary tap water as well as the solvents, surfactants etc. used for the formulation, in corresponding aqueous dilutions, are used as control.

After drying, the slides are put into dishes containing tap water for 5 weeks. On the first day the water is changed 5 times to remove the test substances and later 5 times per week.

For the subsequent activity control in the test on non-embryonated and on embryonated eggs, the percentage of embryonated eggs and of intact embryonation respectively is determined microscopically.

The tests revealed that the active substances have a very good action against *Ascarididae eggs*.

What is claimed is:

1. A method for controlling coccidial diseases which comprises treating oocyst-bearing material excreted by the the animals with an effective amount of a compound of the formula

R—NH—R' wherein
R represents a straight-chain or branched alkyl of from 5 to 18 carbon atoms, or a monocyclic cycloalkyl or monocyclic cycloalkylalkyl of up to 12 carbon atoms and which contains at least 5 carbon atoms in the cyclic moiety, and
R' represents a straight-chain or branched alkyl of from 1 to 9 carbon atoms, monocyclic cycloalkyl of from 3 to 6 carbon atoms, cyclopropylmethyl, cyclohexylmethyl or cyclohexylpropyl,
and wherein R and R' together contain at least 10 carbon atoms, or a salt of said compound with hydrochloric acid, hydrobromic acid, acetic acid, lactic acid, citric acid, sorbic acid, undecylenic acid or glucuronic acid.

2. A method according to claim 1 wherein
R represents unbranched alkyl of from 10 to 12 carbon atoms, and
R' represents straight-chain or branched alkyl of from 1 to 4 carbon atoms or cyclopropylmethyl.

* * * * *